US009173407B2

(12) United States Patent
Igarashi et al.

(10) Patent No.: US 9,173,407 B2
(45) Date of Patent: Nov. 3, 2015

(54) DISEASE RESISTANCE ENHANCER FOR PLANTS AND METHOD OF CONTROLLING PLANT DISEASE BY USING THE SAME

(75) Inventors: Daisuke Igarashi, Kawasaki (JP); Taito Takeda, Kawasaki (JP); Takashi Ishizaki, Kawasaki (JP); Kazuhiko Totsuka, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 164 days.

(21) Appl. No.: 12/833,590

(22) Filed: Jul. 9, 2010

(65) Prior Publication Data

US 2010/0330055 A1 Dec. 30, 2010

(30) Foreign Application Priority Data

Jan. 11, 2008 (JP) ................................ 2008-004833
Aug. 29, 2008 (JP) ................................ 2008-221563

(51) Int. Cl.
*A01N 63/02* (2006.01)

(52) U.S. Cl.
CPC .................................... *A01N 63/02* (2013.01)

(58) Field of Classification Search
CPC .................................................. A01N 63/02
See application file for complete search history.

(56) References Cited

U.S. PATENT DOCUMENTS

| | | | | |
|---|---|---|---|---|
| 6,060,429 | A * | 5/2000 | Ben-Shalom et al. | 514/54 |
| 6,562,757 | B1 * | 5/2003 | Ferrier et al. | 504/127 |
| 7,189,543 | B2 | 3/2007 | Nishi et al. | |
| 8,202,514 | B2 | 6/2012 | Cho et al. | |
| 2011/0262416 | A1 | 10/2011 | Cho et al. | |

FOREIGN PATENT DOCUMENTS

| | | |
|---|---|---|
| CN | 1596658 | 3/2005 |
| JP | 52-076427 | 6/1977 |
| JP | 53-041423 | 4/1978 |
| JP | 05-331016 | 12/1993 |
| JP | 06-080530 | 3/1994 |
| JP | 6-80530 | 3/1994 |
| JP | 2846610 | 10/1998 |
| JP | 11-029412 | 2/1999 |
| JP | 2006-219372 | 8/2006 |
| JP | 2007-70292 | 3/2007 |
| JP | 2007-070292 | 3/2007 |
| JP | 2007-77065 | 3/2007 |
| JP | 2007-077065 | 3/2007 |
| JP | 2007-530032 | 11/2007 |
| JP | 2008004833 A2 * | 1/2008 |
| JP | 2008221563 A2 * | 9/2008 |
| WO | WO 98/47364 | 10/1998 |
| WO | WO 2005/090553 | 9/2005 |

OTHER PUBLICATIONS

Schleifer et al., "Peptidoglycan Types of Bacterial Cell Walls and their Taxonomic Implications", Bacteriological Reviews 36 (4) 407-477 (1972).*

Igarashi et al., "Glutamate Fermentation By-product Activates Plant Defence Responses and Confers Resitance Against Pathogen Infection", J. Phytopathol. 158 : 668-675 (2010).*

Schleifer et al., "Peptidoglycan Types of Bacterial Cell Walls and their Taxonomic Implications", Bacteriological Reviews 36 (4) 407-477 (1972). :.*

Newman et al., "Lipoplysaccharide from Xanthomonas campestris Induces Defense-Related Gene Expression in Brassica campestris", Molecular Plant-Microbe Interactions 8 (5) : 778-780 (1995).* http://3272.id.all.biz/ajifol-fertilizer-g18726, AJIOL fertilizer posted Jan. 19, 2012, accessed Aug. 25, 2014, 1 page.*

PT Ajinomoto Indonesia Co. "AJIFOL Fertilizer" <URL:http://3272.id.all.biz/ajifol-fertilizer-g18726>, Jan. 19, 2012, accessed online Aug. 25, 2014, 1 page.*

Gust, A. A., et al., "Bacteria-derived Peptidoglycans Constitute Pathogen-associated Molecular Patterns Triggering Innate Immunity in Arabidopsis," J. Biol. Chem. 2007;282(44):32338-32348.

Keen, N. T., "The molecular biology of disease resistance," Plant Mol. Biol. 1992;19:109-122.

Koga, J., et al., "Cerebrosides a and C, Sphingolipid Elicitors of Hypersensitive Cell Death and Phytoalexin Accumulation in Rice Plants," J. Biol. Chem. 1998;273(48):31985-31991.

Koga, J., et al., "Cholic Acid, a Bile Acid Elicitor of Hypersensitive Cell Death, Pathogenesis-Related Protein Synthesis, and Phytoalexin Accumulation in Rice," Plant Physiol. 2006;140:1475-1483.

Newman, M-A., et al., "Prior exposure to lipopolysaccharide potentiates expression of plant defenses in response to bacteria," The Plant Journal 2002;29(4):487-495.

Nojiri, H., et al., "Involvement of Jasmonic Acid in Elicitor-Induced Phytoalexin Production in Suspension-Cultured Rice Cells," Plant Physiol. 1996;110:387-392.

Sharp, J. K., et al., "Purification and Partial Characterization of a 13-Glucan Fragment That Elicits Phytoalexin Accumulation in Soybean," J. Biol. Chem. 1984;259(18):11312-11320.

Sharp, J. K., et al., "The Primary Structures of One Elicitor-active and Seven Elicitor-inactive Hexa(β-D-glucopyranosyl)-D-glucitols Isolated from the Mycelial Walls of *Phytophthora megasperma* f. sp. glycinea," J. Biol. Chem. 1984;259(18):11321-11336.

Yamada, a., et al., "Induction of Phytoalexin Formation in Suspension-cultured Rice Cells by N-Acetylchitooligosaccharides," Biosci. Biotech. Biochem. 1993;57(3):405-409.

Yamaguchi, T., et al., "Differences in the Recognition of Glucan Elicitor Signals between Rice and Soybean: PGlucan Fragments from the Rice Blast Disease Fungus *Pyricularia oryzae* That Elicit Phytoalexin Biosynthesis in Suspension-Cultured Rice Cells," The Plant Cell 2000;12:817-826.

Technical Report (CJE14-2013) for Peruvian Patent App. No. 000027-2009/DIN.

(Continued)

*Primary Examiner* — Rosanne Kosson
*Assistant Examiner* — Aaron J Kosar
(74) *Attorney, Agent, or Firm* — Shelly Guest Cermak; Cermak Nakajima & McGowan LLP

(57) ABSTRACT

Infection of pathogens is controlled by inducing disease resistance with a method of treating a plant with a composition of an acidic heat-treated solution of microorganisms.

7 Claims, 8 Drawing Sheets

(56) References Cited

OTHER PUBLICATIONS

Britz-Mckibbin, P., et al., "Picomolar analysis of flavins in biological samples by dynamic pH junction-sweeping capillary electrophoresis with laser-induced fluorescence detection," Analytical Biochem. 2003;313:89-96.

Supplementary European Search Report for European Patent App. No. 09700633.2 (Jul. 18, 2013).

International Search Report for PCT Patent App. No. PCT/JP2009/050216 (Feb. 3, 2009).

* cited by examiner (A)

control liquid

*Corynebacterium* acid- and heat-treated liquid (B)

DISEASE RESISTANCE ENHANCER FOR PLANTS AND METHOD OF CONTROLLING PLANT DISEASE BY USING THE SAME

This application is a continuation under 35 U.S.C. §120 of PCT Patent Application No. PCT/JP2009/050216, filed Jan. 9, 2009, which claims priority under 35 U.S.C. §119 to Japanese Patent Application Nos. 2008-004833, filed on Jan. 11, 2008, and 2008-221563, filed Aug. 29, 2008, which are incorporated in their entireties by reference. The Sequence Listing in electronic format filed herewith is also hereby incorporated by reference in its entirety (File Name: 2010-07-09T_US-438_Seq_List; File Size: 2 KB; Date Created: Jul. 9, 2010).

BACKGROUND OF THE INVENTION

1. Field of the Invention

The present invention relates to a composition containing a disease resistance enhancer for plants. The enhancer is produced by using a microorganism, which is environmentally friendly and is safe for users and consumers. The present invention also relates to a method for controlling plant diseases.

2. Brief Description of the Related Art

Pesticides that act directly on a pathogen, such as bactericides, are often used to control diseases that afflict crop plants. However, another type of pesticide is known which control crop diseases by enhancing the plants' intrinsic disease resistance, and these are called "resistance induction-type pesticides." Pesticides and bactericides that act directly on plant pathogens often exhibit bactericidal effects against the pathogens. Yet, continuous use of such pesticides often results in mutants which are resistant to the pesticide agents. Alternatively, the resistance induction-type pesticides do not act directly on the pathogens and instead control disease infection by inducing the resistance of the plant to the disease pathogen. Hence, there have been no reports to date of mutants that are resistant to this type of pesticide. Furthermore, because the resistance induction-type pesticides have less bactericidal action against organisms, it is more likely that this type of pesticide will be better for the environment, particularly for organisms other than plants.

Pesticides are known which are marketed for induction of resistance to plant diseases, and include probenazole (trade name: Oryzemate), benzothiazole (BTH)-based acibenzolar S-methyl (ASM, trade name: Bion), thiadiazole carboxamide-based tiadinil (trade name: V-GET).

In addition, known substances derived from natural materials which induce disease resistance include polysaccharide decomposition products (JP 5-331016A), cerebrosides (JP2846610B, WO 98/47364 and Koga J. et. al., J. Biol. Chem., 1998, 48, 27, p. 31985-31991), jasmonic acid (JP 11-29412A and Nojiri H. et. al., Plant Physiol., 1996, 110, p. 387-392), chitin oligosaccharides (Yamada A. et. al., Biosci. Biotech. Biochem., 1993, 57, 3, p. 405-409), β-1,3- and β-1,6-glucan oligosaccharides (Sharp J. K. et al., J. Biol. Chem., 1984, 259, p. 11312-11320, Sharp J. K. et. al., J. Biol. Chem., 1984, 259, p. 11321-11336 and Yamaguchi T. et. al., Plant Cell, 2000, 12, p. 817-826), cholic acid (JP 2006-219372A and Koga J. et. al., Plant Physiol. 2006, 140, p. 1475-1483), peptide glycan (Gust A. A. et. al., J. Biol. Chem., 2007, 2007 in press), lipopolysaccharide (Newman M. A, Plant J. 2002, 29, p. 487-495), and the like. These substances are called elicitors and are known to have certain effects, including causing the accumulation of phytoalexins, which have an antimicrobial activity against pathogens, and causing the accumulation of PR proteins (pathogenesis-related proteins), such as chitinase and β-1,3-glucanase, which digest the cell walls of the pathogens and induce hypersensitive cell death (Yamada A. et. al., Biosci. Biotech. Biochem., 1993, 57, 3, p. 405-409 and Keen N. T., Plant Mol. Biol., 1992, 19, p. 109-122).

Furthermore, a method has been reported for controlling infection by pathogens by spraying the supernatant of a proline fermentation solution by *Corynebacterium* (JP 6-80530A). Yet, the effect of a solution obtained by heat-treating microorganisms under acidic conditions has not been previously reported.

SUMMARY OF THE INVENTION

An aspect of the present invention is to provide a composition that enhances the resistance to disease in plants. This composition is safe for consumers and users, inexpensive, and environmentally friendly. It is another aspect of the present invention to provide a method for controlling plant diseases using such a composition.

It is an aspect of the invention to provide an extract obtained by subjecting microorganisms to a heat-treatment in an acidic solution. This extract was found to be able to induce a high amount of resistance to disease in plants. That is, treatment of plants with this extract induced the production of reactive oxygen and an increase in chitinase and glucanase activity, both of which were found to induce significant resistance to disease. Furthermore, this extract was found to strongly prevent infection of rice blast and *Brassicaceae Pseudomonas syringae* pv. *maculicola*. The addition of a metal such as zinc and/or copper was found to further increase the disease resistance effect by the extract, and maintain the effect for a longer time.

It is an aspect of the present invention to provide a composition comprising a microbial cell extract, wherein said microbial cell has been subjected to a heat treatment in an acidic solution, and wherein the composition is able to induce resistance to disease in plants.

It is a further aspect of the present invention to provide the composition as described above, wherein said heat treatment in an acidic solution comprises treatment at 70° C. or higher in a solution having a pH of 6 or less.

It is a further aspect of the present invention to provide the composition as described above, wherein said microbial cell is selected from the group consisting of *Escherichia* bacteria, Coryneform bacteria, *Pantoea* bacteria, *Bacillus* bacteria, yeast, lactic acid bacteria, and acetic acid bacteria.

It is a further aspect of the present invention to provide the composition as described above, wherein said composition is a foliar spray agent.

It is a further aspect of the present invention to provide the composition as described above, which further contains a metal(s).

It is a further aspect of the present invention to provide the composition as described above, wherein said metal is selected from the group consisting of zinc, copper, and combinations thereof.

It is an even further aspect of the present invention to provide a method for controlling the spread or infection of a plant disease comprising treating a plant with the composition as described above.

It is a further aspect of the present invention to provide the method as described above, wherein said microbial cell is selected from the group consisting of *Escherichia* bacteria, Coryneform bacteria, *Pantoea* bacteria, *Bacillus* bacteria, yeast, lactic acid bacteria, and acetic acid bacteria.

It is a further aspect of the present invention to provide the method as described above, wherein said composition is a foliar spray agent.

It is a further aspect of the present invention to provide the method as described above, which further contains a metal(s).

It is a further aspect of the present invention to provide the method as described above, wherein said metal is selected from the group consisting of zinc, copper, and combinations thereof.

BRIEF DESCRIPTION OF THE DRAWINGS

FIGS. 3A and 3B show the effect on the chitinase activity of *Arabidopsis thaliana*. The activity is shown after spraying onto leaves the following: C) a control (spreading agent alone), or 1) an acidic heat-treated solution.

FIGS. 9A and 9B show the effect on the chitinase activity of *Arabidopsis thaliana*. The activity is shown after spraying onto leaves the following: C) a control (spreading agent alone), FIG. 9A (1) peptide glycan (100 mg/L) and FIG. 9B (1) LPS (100 mg/L).

FIG. 11A is a photograph of leaves of *Arabidopsis thaliana*. The two leaves on the left are untreated (control), whereas the two leaves on the right are infected with a pathogen after being pretreated with the acidic heat-treated solution of *Corynebacterium*.

DESCRIPTION OF THE PREFERRED EMBODIMENTS

Figure 1:
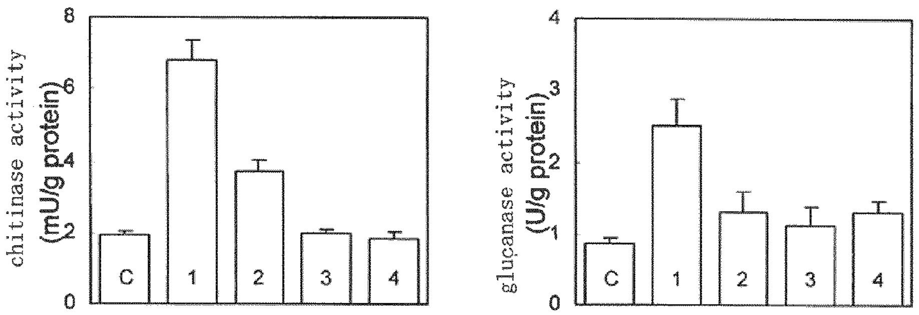
FIG. 1 shows the effect of a treated solution of *Corynebacterium* on the chitinase activity or glucanase activity of *Arabidopsis thaliana*. The activity is shown after spraying onto leaves the following: C) control (spreading agent alone), 1) an acidic heat-treated solution of *Corynebacterium,* 2) a heat-treated solution of *Corynebacterium* without pH adjustment (pH 6.3), and 3) an untreated solution of *Corynebacterium* (pH 6.3).

The microorganisms can be eukaryotes such as yeast or fungi, or prokaryotes such as bacteria or actinomycetes, and can be either gram-positive or gram-negative. Bacteria such as Coryneform, *Bacillus, Escherichia, Pantoea*, lactic acid bacteria, acetic acid bacteria, yeast, or the like can be used.

Examples of Coryneform bacteria include the *Corynebacterium* bacteria such as *Corynebacterium acetoacidophilum, Corynebacterium acetoglutamicum, Corynebacterium alkanolyticum, Corynebacterium ammoniagenes, Corynebacterium callunae, Corynebacterium glutamicum, Corynebacterium lilium, Corynebacterium melassecola, Corynebacterium thermoaminogenes* or *Corynebacterium harculis*; the *Brevibacterium* bacteria such as *Brevibacterium divaricatum, Brevibacterium flavum, Brevibacterium immariophilum, Brevibacterium lactofermentum, Brevibacterium roseum, Brevibacterium saccharolyticum, Brevibacterium thiogenitalis, Brevibacterium album* or *Brevibacterium cerinum*; and the *Microbacterium* bacteria such as *Microbacterium ammoniaphilum.*

An example of *Escherichia* bacteria includes *Escherichia coli* (*E. coli*).

An example of *Pantoea* bacteria includes *Pantoea ananatis.*

Examples of *Bacillus* bacteria include *Bacillus subtilis, Bacillus amyloliquefaciens*, and *Bacillus pumilus.*

Examples of yeast include *Saccharomyces* yeast such as *Saccharomyces cerevisae; Pichia* yeast such as *Pichia pastoris; Hansenula* yeast such as *Hansenula polymolpha; Candida* yeast such as *Candida utilis*; and *Schizosaccharomyces* yeast such as *Schizosaccharomyces pombe.*

Examples of lactic acid bacteria include the *Lactobacillus* bacteria such as *Lactobacillus casei, Lactococcus* bacteria such as *Lactococcus lactic*, and *Bifidobacterium* bacteria such as *Bifidobacterium bifidum.*

An example of acetic acid bacteria includes *Acetobacter* bacteria such as *Acetobacter aceti.*

The acidic heat-treatment can be carried out in an acidic solution having a pH of 6 or less, or in another example, a pH of 5 or less, or in another example, a pH of 4 or less, and in yet another example, a pH of 3 or less. The lower limit is not restricted, but an example is a pH of 1. The heating conditions are not limited, but are generally carried out in the range of 70° C.-200° C. In one example, the heat treatment be carried out at 75° C. or higher, or in another example, 90° C. or higher, or in another example, 100° C. or higher, and yet in another example, 120° C. or higher. The heat-treatment can be carried out usually for 1 to 120 minutes, or in another example, for 10 to 60 minutes.

The heat-treatment can be carried out after suspending the microbial cells in water, a buffer, or a medium, and then acidifying the resulting suspension. Also, the heat-treatment may be carried out after acidifying the culture medium containing the microbial cells upon completion of the culture. For instance, the heat-treatment may be carried out after acidifying the culture medium (fermentation solution) containing the microbial cells, when the microbial cells were used to produce substances such as amino acids by fermentation. Furthermore, the heat-treatment may be carried out after suspending an organic sludge containing microorganisms, or the like, in water or buffer, and acidifying the resulting suspension. Examples of organic sludge includes sewage sludge discharged from a common sewage treatment facility, sludge discharged after biological treatment of various organic wastewater, as well as excess sludge and dewatered products thereof. When the acidic heat-treatment is carried out, the microbial cells can be suspended at a concentration of 50 mg-200 g (dry weight)/L.

An extract obtained by an acidic heat-treatment of a microorganism (hereinafter referred to as acidic heat-treated solution) can be used in a composition which contains an enhancer of resistance to disease after removal of the bacterial cells by centrifugation, membrane separation or the like, or can be used without removing the bacterial cells.

The concentration of the composition containing an enhancer of resistance to disease when applied to a plant can be adjusted by diluting or concentrating to an appropriate concentration depending on the type of plant, the growth stage of the plant, or the method of application. In addition, a fraction resulting from fractionation by molecular weight can be used.

The activity to induce plant disease resistance can mean a series of reactions resulting in the production of reactive oxygen, the accumulation of antibacterial proteins and antibacterial compounds, and the strengthening of the cell wall and accumulation of bactericidal enzymes, such as chitinase and glucanase. When infected by bacteria, filamentous bacteria, or the like, plants often trigger the above series of reactions to control the spread of the infection. The activity of inducing plant resistance can be evaluated by measuring the enzymatic activity of chitinase or glucanase and measuring the reactive oxygen according to the methods described in the Examples section of this specification. In addition, the amount of expression of a disease resistance-related gene such as the PBZ1 gene using RT-PCR or the like can be measured.

Examples of methods for applying the composition containing an enhancer of disease resistance include spraying a plant body (foliar spray agent or the like), spreading the composition onto a plant body, dipping the plant roots, and mixing the composition into the soil in which the plant is growing. Also, because the method for controlling plant diseases primarily prevents diseases, the application method can be used prior to the outbreak of the disease. Yet, even after the outbreak of the disease, spreading of the disease can be blocked and prevented by application of the composition.

The composition containing an enhancer of disease resistance can contain other ingredients. Examples of these other ingredients include metals such as zinc and copper. Although spraying the composition containing the acidic heat-treated solution of microorganisms alone can exert the effect, the addition of metals such as zinc and copper can enhance or prolong the effect of enhancing disease resistance. The concentration of the metal can be in the range of 0.0001%-10% (w/v) (for metal weight) at the time of the application. The metals such as zinc and copper can be in the form of salts so as to form ions once added to the solution.

The crops that can benefit from application of the composition containing an enhancer of disease resistance are not particularly limited, and can include any cultivated plant. Examples include the *poaceae* plants, such as rice, barley, wheat, corn, oat or lawn grass; the *solanaceae* plants, such as tomato, eggplant or potato; the *cucurbitaceae* plants, such as cucumber, melon or pumpkin; the *leguminosae* plants, such as pea, soybean, kidney bean, alfalfa, peanut, fava bean; the *brassicaceae* plants, such as daikon radish, Chinese cabbage, cabbage, komatsuna, rape blossoms, bok choy or *Arabidopsis thaliana*; the *rosaceae* plants (such as strawberry, apple or pear), the *moraceae* (such as mulberry), the *malvaceae* (such as cotton), the *umbelliferae* (such as carrot, parsley or celery), the *liliaceae* (such as green onion, onion or asparagus), the *compositae* (such as burdock, sunflower, chrysanthemum, crown daisy, safflower, lettuce) and the *vitaceae* (such as grape).

Since the reaction which gives rise to plant disease resistance is generally nonspecific to pathogens, plant diseases caused by fungus, bacteria, and viruses can benefit from application of the composition. Examples include diseases caused by *Magnaporthe grisea, Cochliobolus miyabeanus, Pseudomonas syringae* pv. *maculicola, Spongospora subterranea, Phytophthora infestans, Peronospora manshurica, Eryshiphe graminis* f. sp. hordei, *Eryshiphe graminis* f. sp. tritici, *Gibberella zeae, Mycosphaerella pinodes, Sclerotinia borealis, Puccinia recondita, Ustilago maydis, Ceratobasidium gramineum, Rhizoctonia solani, Rhizoctonia solani, Alternaria solani, Cercospora kikuchii, Fusarium oxysporum* f. sp. batatas, *Fusarium oxysporum* f. sp. melonis, *Fusarium oxysporum* f. sp. lactucae, *Fusarium oxysporum* f. sp. lycopersici, *Fusarium oxysporum* f. sp. spinaciae, *Verticillium dahliae, Plasmodiophora brassicae, Pythium debaryanum, Botrytis cinerea, Colletotrichum phomoides, Hordeum vulgare, Pseudomonas syringae* pv. *syringae, Erwiniasubsp. atroseptica, Xanthomonas campestris* pv. *oryzae, Streptomyces scabies*, Soil-borne wheat mosaic virus, Soybean mosaic virus, Alfalfa mosaic virus and Potato leafroll virus.

The composition containing the enhancer of disease resistance can be used on plants in any form, such as a solution, powder, granule, emulsion, wettable powder, oil, aerosol, flowable by mixing the acidic heat-treated solution of microorganisms with appropriate additives. Furthermore, optionally, the pH of the composition can be adjusted by adding buffer. The ability of the composition to penetrate the plant can be modified by adding a spreading agent, surfactant or the like.

EXAMPLES

The present invention will now be described specifically by way of the following non-limiting examples.

Example 1

Method for Preparing Disease Resistance Enhancer for Plants Derived from Microorganisms

*Escherichia coli, Corynebacterium glutamicum, Pantoea ananatis, Bacillus subtilis* and *Saccharomyces cerevisiae* were used as the microbial cells. Each type of bacterial cells was cultured to about 1.5-2.0 g (dry weight) per 100 mL of culture medium. For culturing, the medium described in JP 2005-278643, JP 2003-259861, WO01/090310 or the like was used.

The bacterial cells were collected by centrifugation at 6000 rpm, washed with water three times and then suspended in 100 ml of water per 1.5-2.0 g (dry weight). $H_2SO_4$ was added to adjust to a pH of 3.2, and then subjected to heat-treatment using an autoclave at 121° C. for 30 minutes. The resulting solution was centrifuged at 10,000 rpm to remove insoluble materials. The obtained supernatant was used in the experiments below as the "acidic heat-treated solution". Unless otherwise described, a 100-fold diluted solution was used to treat plants.

Example 2

Evaluation of Plant Disease Resistance Induction Using Enzymatic Activity as Index (1) Method of Cultivation of Plant and Spraying Cultivation on agar of *Arabidopsis thaliana* was carried out in a medium containing OptMS inorganic salt culture medium (Table 1) supplemented with 1% sucrose and 0.8% agar. Plants cultivated for 2 weeks were used. The cultivation was carried out with a diurnal cycle of a light period of 16 hours at the light intensity of about 70 μmol $m^{-2}$ $s^{-1}$. For cultivation on rock wool of *Arabidopsis thaliana*, rock wool of 5 cm square (manufactured by Nittobo, size V) was used. As a fertiliser, OptMS inorganic salt culture medium (Table 1) was used. The cultivation was carried out with a diurnal cycle of a light period of 14 hours at light intensity of about 100 μmol $m^{-2}$ $s^{-1}$ for 21 days. Among aerial parts, all but leaf petioles were used as samples. The spraying effects of each solution were evaluated for a plant cultivated on the agar medium or rock wool. Unless otherwise described, the plant was treated with a 100-fold dilution of the solution prepared by the method described in Example 1 to measure the enzymatic activity in leaves 24 hours after the treatment. A 1000-fold diluted concentration of APPLAUCH BI (Kao Corporation) was added as a spreading agent to the spray solution.

TABLE 1

| | |
|---|---|
| $KPO_4$ (pH 5.7) | 2.5 mM |
| $MgSO_4$ | 2 mM |
| $Ca(NO_3)_2$ | 3 mM |
| $NH_4NO_3$ | 2.5 mM |
| $KNO_3$ | 2 mM |
| KCl | 2 mM |
| micro nutrients | |
| Fe(III)-EDTA | 0.1 mM |
| $MnCl_2$ | 0.1 mM |
| $CuSO_4$ | 0.5 μM |
| $ZnSO_4$ | 30 μM |
| $NaMoO_4$ | 1 μM |
| $CoCl_2$ | 0.1 μM |
| $H_3BO_3$ | 0.1 mM |
| NaCl | 10 μM |

(2) Extraction of Enzyme

Immediately after the plant was sampled for measurement of the enzymatic activity, the samples were frozen with liquid nitrogen and stored at −80° C. The frozen samples were disrupted using plant Mixer Mill MM300 (QIAGEN) and dissolved in 500 μL of an extraction buffer [100 mM $Na_3PO_4$ (pH 6.0), 1 mM DTI', protease inhibitor/complete mini EDTA free (Roche)]. After centrifugation at 10,000 rpm for 5 minutes, the supernatant was passed through a 0.22 μm filter to remove insoluble materials. The resulting solution was passed through an ultrafiltration filter UFV5BG00 (Millipore) to further concentrate and desalt. Desalting was performed by passing 1.5 ml of the extraction buffer three times. The thus obtained fraction was used as a crude extract fraction, which was subjected to measurement of protein concentration by the Bradford method and then used to measure the enzymatic activity.

(3) Measurement of Chitinase Activity

The chitinase activity was determined by the method by McCreath et al. (J. Microbiol. Methods 14:229-1992). A substrate 4MU-$(GlcNAc)_3$ (SIGMA M5639) was dissolved in 50% ethanol to a final concentration of 0.4 mM and stored at −20° C. When used, it was diluted 10-fold to obtain a substrate solution. The crude extract solution was adjusted to 6-8 μg/μL and 50 μL of the solution was used for the reaction. After preincubation on a 96-well plate at 37° C. for 10 minutes, 50 μL of the substrate solution was added and the reaction was initiated at 37° C. 30 minutes and 150 minutes after the beginning of the reaction, 100 μL of 1 M Gly/NaOH buffer (pH 10.2) was added to the reaction mixture to terminate the reaction. The reaction and termination were carried out on a 96-well plate with a final volume of 200 μL. Bubbles on the solution surface were completely removed and the fluorescence intensity was then measured using a plate reader for fluorescence detection (WALLAC 1420 ARVO-SX). Measurement of fluorescence was performed employing 360 nm for excitation and 450 nm for emission. The reaction amount was based on a standard value determined using 4-MU (methylumbelliferone) as a substrate, and the amount of enzyme which reacted with 1 μmol for 1 minute was defined as 1 unit.

(4) Measurement of Glucanase Activity

Measurement of a glucanase activity in *Arabidopsis thaliana* was carried out in accordance with the method by Aono et al. (Appl Environ Microbiol. 58:520-1992). A method for breaking up laminarin which is a soluble polysaccharide was employed. A substrate, laminarin (SIGMA L9634) was dissolved in sterilized water to a final concentration of 5 mg/ml and stored at −20° C. The crude extract solution was adjusted to 6-8 μg/μL and 50 μL of the solution was added to 50 μL of the substrate solution to start the reaction at 37° C. 180 minutes and 360 minutes after the start of the reaction, 100 μL of the reaction mixture was added to 500 μL of DNS solution (5 g/L dinitrosalicylic acid, 16 g/L NaOH, 300 g/L potassium sodium tartrate tetrahydrate) and the mixture was heated at 98° C. for 10 minutes and then rapidly cooled on ice to develop color. The DNS method was carried out by the method by Miller et al. (Anal Chem 31: 426-1959). After the coloring, the activity was determined based on absorbance at 540 nm. The reaction amount was based on a standard value determined using glucose as a substrate, and the amount of enzyme which reacted with 1 μmol for 1 minute was defined as 1 unit.

Figure 2:
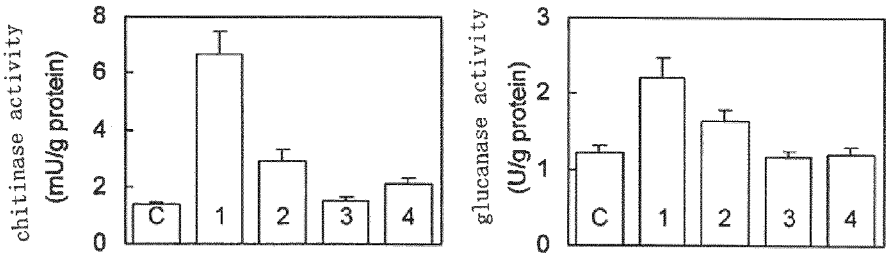
FIG. 2 shows the effect of a treated solution of *E. coli* on the chitinase activity or glucanase activity of *Arabidopsis thaliana*. The activity is shown after spraying onto leaves the following: C) a control (spreading agent alone), 1) an acidic heat-treated solution of *E. coli,* 2) a heat-treated solution of *E. coli* without pH adjustment (pH 6.3), and 3) an untreated solution of *E. coli* (pH 6.3).
Figure 3:
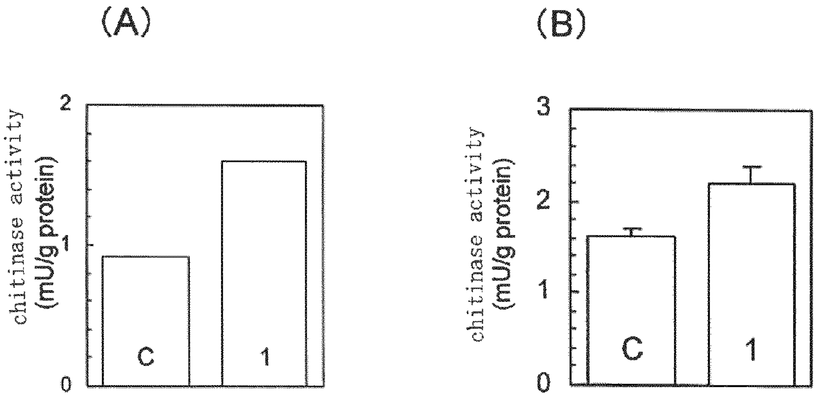
FIG. 3A shows the effect of a treated solution of *Bacillus* and FIG. 3B shows the effect of a treated solution of *Pantoea*. Both

The results of the evaluation of the plant sprayed with the acidic heat-treated solution of *Corynebacterium* cells are shown in FIG. 1. Compared with bacterial cells that were subjected to only heat or acid treatment, spraying the solution subjected to heat and acid was found to drastically increase the chitinase/glucanase activity. The results of the evaluation carried out using *E. coli* cells are shown in FIG. 2. Similar to the evaluation with *Corynebacterium*, the heat-treatment under acidic conditions resulted in very effective extraction of substances that induce disease resistance. Similarly, heat-treated solutions of *Pantoea* or *Bacillus* cells under acidic conditions were evaluated. As shown in FIG. 3, in both cases, an increase in the chitinase activity was observed, indicating both had the effect of inducing disease resistance.

Figure 4:
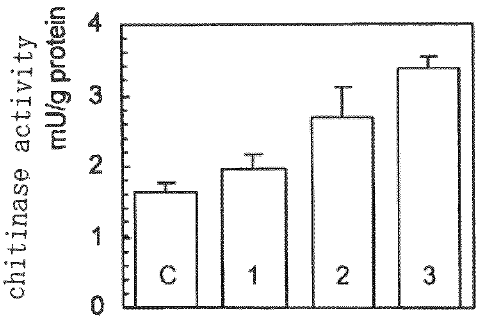
FIG. 4 shows the effect of a treated solution of *Corynebacterium* on the chitinase activity of *Arabidopsis thaliana*. The activity is shown after spraying onto leaves the following: C) a control (spreading agent alone), 1) a suspension of *Corynebacterium* cells (pH 6), 2) a solution where the suspension of *Corynebacterium* cells (pH 6) was heat-treated at 75° C. for 60 minutes, or 3) a solution where the suspension of *Corynebacterium* cells (pH 6) was heat-treated at 95° C. for 60 minutes. In this experiment, the effect of the heat treatment was examined using a solution of bacterial cells which had been diluted 10-fold.

The results of the evaluation of a plant sprayed with a composition containing *Corynebacterium* cells obtained by heat treatment at pH 6 are shown in FIG. 4. As a result, even with the solution obtained by heating at pH 6 and 75° C., an increase in the chitinase activity was observed, indicating the solution had the effect of inducing disease resistance.

Figure 5:
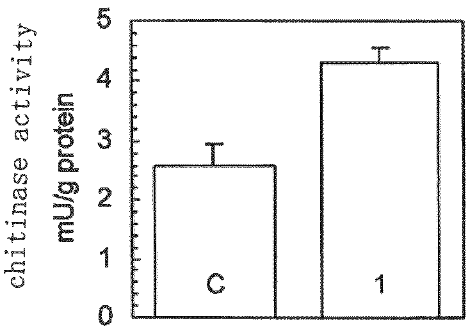
FIG. 5 shows the effect of a treated solution of activated sludge on the chitinase activity of *Arabidopsis thaliana*. The activity is shown after spraying onto leaves the following: C) a control (spreading agent alone), or 1) a 20-fold diluted treated solution of activated sludge.

In addition, excess sludge produced from an activated sludge treatment apparatus for industrial effluent containing, as a major ingredient, amino acid fermentation waste was dewatered. The resulting sludge was added to an aqueous $H_2SO_4$ solution, adjusted to pH 3.2 and then subjected to a heat treatment of 121° C. for 20 minutes. The solution was then centrifuged at 10,000 rpm and the insoluble ingredients were removed. The results using this supernatant are shown in FIG. 5. As a result, it was found that the acidic heat-treated solution of microorganisms contained in the excess sludge also had the effect of inducing disease resistance.

From these results, it was found that treating various microbial cells with heat under acidic conditions resulted in the extraction of substances that are able to induce disease resistance.

Figure 6:
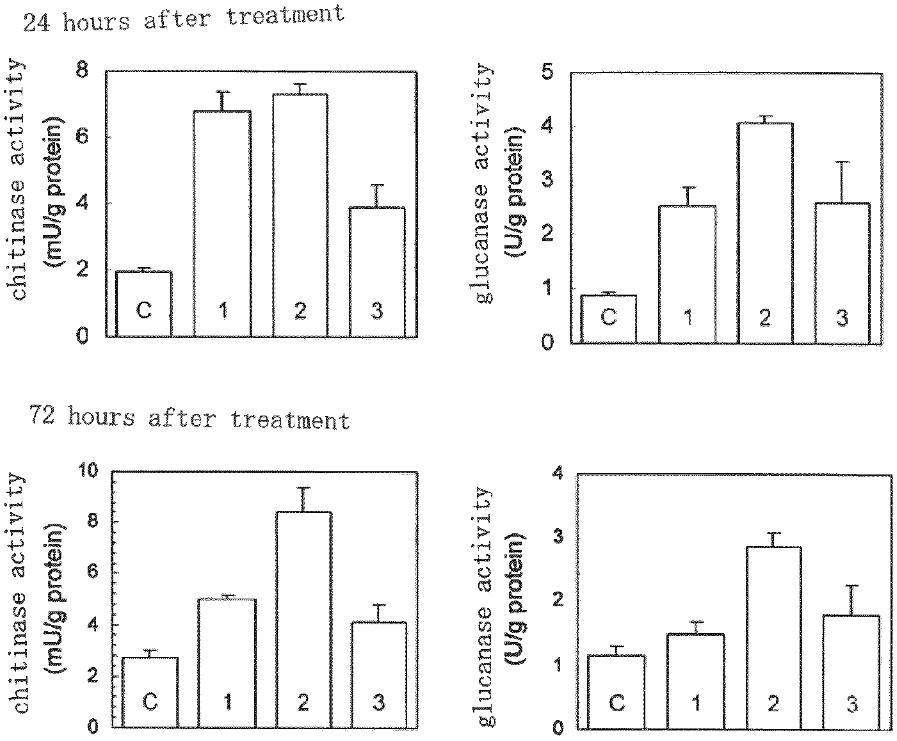
FIG. 6 shows the effect of a treated solution of *Corynebacterium* and zinc on a chitinase activity or glucanase activity of *Arabidopsis thaliana*. The activity is shown after spraying onto leaves the following: C) a control (spreading agent alone), 1) an acidic heat-treated solution of *Corynebacterium,* 2) an acidic heat-treated solution of *Corynebacterium*+zinc (0.01% w/v), or 3) zinc (0.01% w/v). The upper charts show the results at 24 hours after the treatment, and the lower charts show the results at 72 hours after the treatment.
Figure 7:
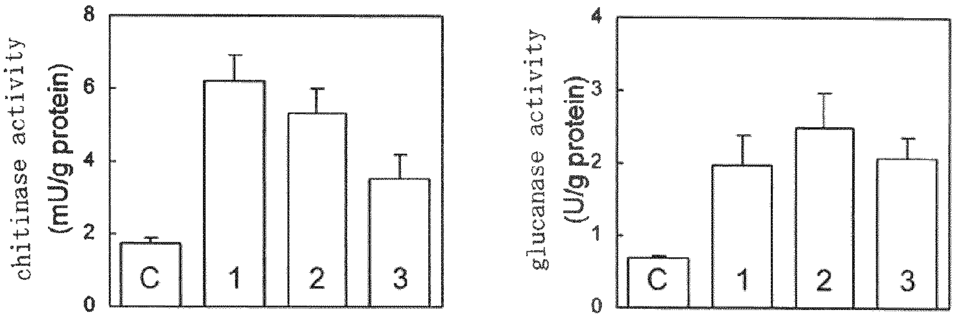
FIG. 7 shows the effect of a treated solution of *E. coli* and zinc on the chitinase activity or glucanase activity of *Arabidopsis thaliana*. The activity is shown after spraying onto leaves the following: C) a control (spreading agent alone), 1) an acidic heat-treated solution of *E. coli,* 2) an acidic heat-treated solution of *E. coli*+zinc (0.01% w/v), or 3) zinc (0.01% w/v).

FIGS. 6 and 7 show experiments where $ZnSO_4$ was mixed in the spray solution to a weight ratio of Zn of 0.01%. When comparing the acidic heat-treated solution of bacterial cells alone or Zn alone, the increase in the enzymatic activity was stronger with the combination of the acidic heat-treated solution of bacterial cells with Zn. This effect was observed both in *Corynebacterium* (FIG. 6) and *E. coli* (FIG. 7) cells, and in particular, the effect on the glucanase activity was significant. Furthermore, the effect at 72 hours was more significant than that at 24 hours, indicating that the addition of Zn was effective to sustain the effect for a long time.

Figure 8:
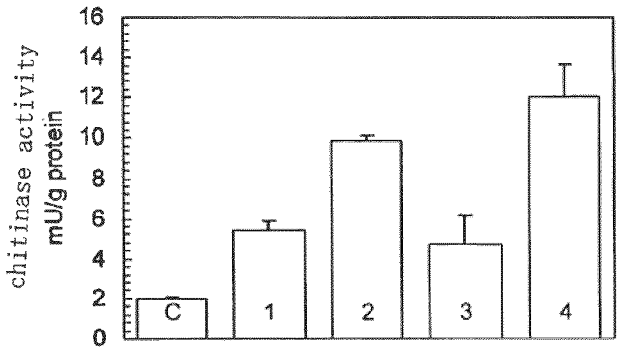
FIG. 8 shows the effect of a treated solution of *Corynebacterium* or *E. coli* and copper on the chitinase activity of *Arabidopsis thaliana*. The activity is shown after spraying onto leaves the following: C) a control (spreading agent), 1) an acidic heat-treated solution of *Corynebacterium,* 2) an acidic heat-treated solution of *Corynebacterium*+Cu (0.01% w/v), 3) an acidic heat-treated solution of *E. coli*, or 4) an acidic heat-treated solution of *E. coli*+Cu (0.01% w/v).

The results of the evaluation with $CuSO_4$ mixed in the spray solution to a weight ratio of Cu of 0.01% are shown in FIG. 8. As a result, when Cu was added to various acidic heat-treated solutions of bacterial cells, the increase in the enzymatic activity was even greater.

Figure 9:
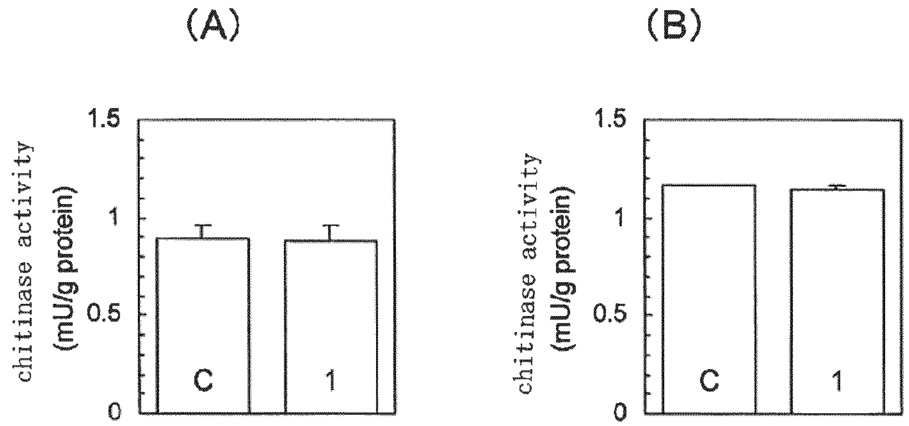
FIG. 9A shows the effect of peptide glycan and FIG. 9B shows the effect of LPS. Both

Comparative Example of Effects of Known Substance which Induce Disease Resistance It has been previously reported that peptide glycan and lipopolysaccharide (LPS), which make up bacterial cell walls, were recognized by plants and induced disease resistance. The effects of these known inducers were compared to those described above. A standard sample of peptide glycan manufactured by InvivoGen (PGN-ECndss ultrapure) was used, and a standard sample of lipopolysaccharide manufactured by Sigma (L8643) was used. Each of these samples was sprayed onto leaves of *Arabidopsis thaliana* at the reported effective concentration of 100 mg/L, and 24 hours later an enzymatic activity was measured. As shown in FIG. 9, no increase in chitinase activity was observed. It was thus found that the induction of disease resistance with the acidic heat-treated solution of bacterial cells was significantly greater than that induced by the known inducer substances.

Figure 10:
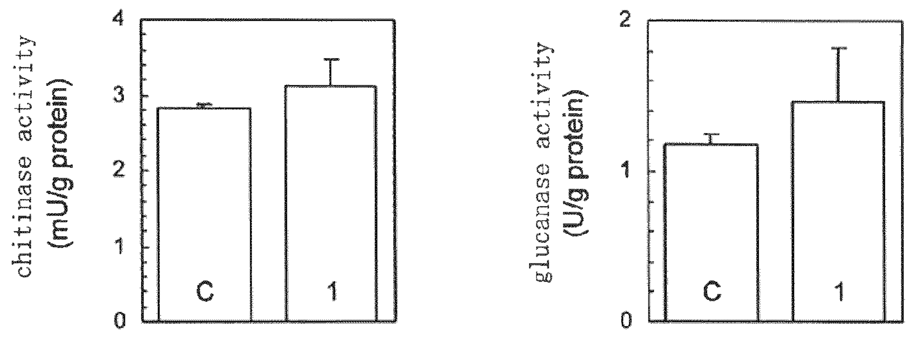
FIG. 10 shows the effect of a supernatant from a proline fermentation solution (amino acid 50 ppm) on a chitinase activity or glucanase activity of *Arabidopsis thaliana*. The activity is shown after spraying onto leaves the following: C) a control (spreading agent alone), or 1) the supernatant of a proline fermentation solution (amino acid 50 ppm).

Also, it had been previously reported that spraying a supernatant of a proline (Pro) fermentation solution could control infection of pathogens (JP 6-80530). Therefore, this was examined and compared to the acidic heat-treated solution of bacterial cells. Proline-producing bacterial cells (*Corynebacterium glutamicum* ATCC21159) were cultured by a method described in JP 6-80530. Amino acids were analyzed using an amino acid analyzer (Hitachi, Ltd., L-8800). To treat plant bodies, a solution diluted such that the total amount of amino acids was 50 ppm was used. As shown in FIG. 10, no significant increase in the enzymatic activity was observed when the supernatant of the Proline fermentation solution was sprayed onto the leaves.

Example 3

Controlling Infection of *Pseudomonas syringae* pv. *maculicola* in *Arabidopsis thaliana*

A pathogen, *Pseudomonas syringae* pv. *maculicola*, was cultured in YEP medium for 24 hours. After the culturing, bacterial cells were collected at 3,000 rpm and suspended in 10 mM $MgSO_4$ solution to $5\times10^6$ cfu/mL. The bacterial cell suspension was infiltrated into leaves with a 1 mL syringe without a needle. Three days later, it was confirmed that the leaves were infected.

Figure 11:
FIGS. 11A and B show the control effect of an acidic heat-treated solution of *Corynebacterium* on the infection of *Pseudomonas syringae* pv. *maculicola* to *Arabidopsis thaliana*.
FIG. 11B is a graph showing the colony forming unit per fresh weight of the leaf.
Figure 11:
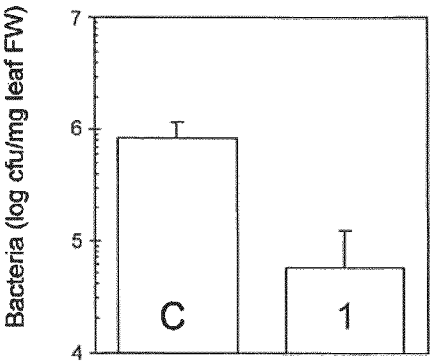

In the test, pretreatment was carried out by spraying a spreading agent alone, or spraying the spreading agent with an acidic heat-treated solution. 24 hours later, the pathogen was added. As shown in FIG. 11, it was found that the infection was significantly inhibited with the spreading agent with the acidic heat-treated solution, compared with the spreading agent alone.

Example 4

Induction of Disease Resistance in Rice and the Effect on Rice Blast Infection (1) Method of Cultivation of Rice and Spraying Rice (variety: Nipponbare) seeds were immersed in water for three days to stimulate germination, seeded in molding for horticulture (4:1 mixture of Power Soil (Kanto Hiryou Industries (Kureha Chemical Industries)) and vermiculite (S.K.Agri)) and cultivated in a green house. Cultivation took place for 14 days under natural light in the green house, and a plant having a foliar age of 4.5 true leaves was used as a sample.

(2) Measurement of Glucanase Activity

Glucanase activity in rice was measured by the method of Inui et al. (Biosci Biotechnol Biochem. 61:975-1997). 2 μL of the sample (acidic heat-treated solution) was placed on each of ten sites on the surface of the fourth true leaf of a plant having a foliar age of 4.5 true leaves. The leaf was frozen 24 hours later using liquid nitrogen and subjected to homogenization extraction. To 100 μL of the crude extract solution, 900 μL of the substrate solution (1% Curdlan (SIGMA C7821), 50 mM $Na_2HPO_4$-citric buffer, (pH5.0)) was added to initiate a reaction at 37° C. 60 minutes after the start of the reaction, 50 μL of the reaction mixture was added to 200 μL of DNS solution (5 g/L dinitrosalicylic acid, 16 g/L NaOH, 300 g/L potassium sodium tartrate tetrahydrate), and the mixture was heated at 98° C. for 10 minutes and then rapidly cooled on ice to develop color. The DNS method was carried out according to Miller et al. (Anal Chem 31:426-1959). After the coloring, the activity was determined based on absorbance at 540 nm. The reacting amount was based on a standard value determined using glucose as a substrate, and the amount of enzyme that reacted with 1 μmol for 1 minute was defined as 1 unit.

Figure 12:
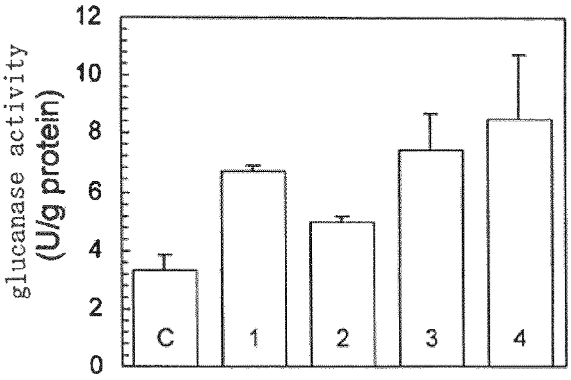
FIG. 12 shows the effect of acidic heat-treated solutions of each microorganism on the chitinase activity of rice. The activity is shown after spraying onto leaves the following: C) a control (spreading agent alone), 1) an acidic heat-treated solution of *Corynebacterium,* 2) an acidic heat-treated solution of *E. coli,* 3) an acidic heat-treated solution of *Pantoea*, or 4) an acidic heat-treated solution of *Bacillus.*

The rice was treated with a solution of *Corynebacterium* cells which had been heat-treated under acidic conditions and prepared in accordance with the method described in Example 1, and applied without being diluted. The glucanase activity was measured after 24 hours. As shown in FIG. 12, the glucanase activity significantly increases when sprayed with the acidic heat-treated solution of the bacterial cells, compared with the control.

(3) Control Effect on Rice Blast Infection in Rice

Figure 13:
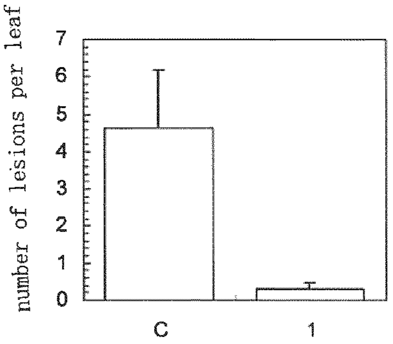
FIG. 13 shows the control effect of an acidic heat-treated solution of *Corynebacterium* on infection of rice blast. Pretreatment was done using C) a control (spreading agent APPLAUCH BI (Kao Corporation)), or 1) an acidic heat-treated solution of *Corynebacterium* was added to the spreading agent. The y-axis on the graph indicates the number of the lesions per leaf.

A sample of the acidic heat-treated solution of *Corynebacterium* cells prepared in accordance with the method described in Example 1 and diluted 10-fold was sprayed on an entire leaf of rice having a foliar age of 4.5 true leaves. After a 24-hour cultivation, a conidial suspension ($1\times10^5$ conidia/mL) of rice blast pathogen (scientific name: *Magnaporthe oryzae*) was sprayed on the leaf. After spraying, the sample was left to stand for 24 hours in a dark, humid room to infect with the rice blast pathogen. Six days after the infection, a preventive value was calculated by measuring the number of susceptible lesions that appeared on the fourth true leaf of each treatment group. The preventive value was calculated as follows: preventive value=(mean of the number of lesions in the control group−mean of the number of lesions in each group treated with a sample/mean of the number of lesions in the control group)×100. As shown in FIG. 13, it was found that, compared with the control group, the spraying of the acidic heat-treated solution of bacterial cells was able to significantly control pathogenic infection.

Example 5

Evaluation of Induction of Disease Resistance using the Production of Reactive Oxygen as an Index in Various Plants Each plant was seeded in soil-Metromix (Hyponex Japan Co., Ltd.) and cultivated at a light intensity of about 100 μmol $m^{-2}$ $s^{-1}$ with a cycle of a 14-hour light period and a 10-hour dark period at 23° C. for 21 days. Fresh true leaves were used for evaluation.

Reactive oxygen ($H_2O_2$) was measured by a method modified from the method of Kunze et al. (Plant Cell, 16, 3496-2004). A 3 mm square of the plant leaf was cut out, and immersed in sterilized water overnight. Then, the resulting samples were transferred to an aqueous solution containing an acidic heat-treated solution of each of the following bacterial cells: 1. *Corynebacterium,* 2. *E. coli,* 3. *Bacillus,* 4. *Pantoea,* 5. *Saccharomyces cerevisiae*, to generate $H_2O_2$. The aqueous solution was added to a reaction solution (50 mM phosphate buffer (pH 5.8), 5 μM Amplex Red (Invitrogen), 1 μg/mL horseradish peroxidase (Sigma Aldrich P8515) and measured at excitation 544 nm and emission 590 nm. Each experiment was run through at least four repetitions and judged in accordance with the following criteria:

Method for Judgment:

1) In each experiment, when the mean value increased not less than 5 fold as compared with the control, a score of +2 was assigned, and when the mean value increased not less than 2 fold as compared with the control, a score of +1 was assigned;

2) In each experiment, a significant test was carried out, and when the p value was <0.01, a score of +2 was assigned, and when the p value was <0.05, a score of +1 was assigned;

3) The sum was divided by the number of the experiments, and a result of not less than 1 was indicated as "++", and a result of not less than 0.5 was indicated as "+)"

As shown in Table 2, the generation of reactive oxygen was confirmed in various plants. It was therefore considered that the induction of disease resistance by the treatment of acidic heat-treated solution of bacterial cells was not species specific.

Table 2 shows the results of the measurement of the generation of the reactive oxygen from the leaf specimen by acidic heat-treated solution of *Corynebacterium glutamicum* (1), *E. coli* (2), *Bacillus subtilis* (3), *Pantoea ananatis* (4) and *Saccharomyces cerevisiae* (5). Also, "n.d." means "not determined."

TABLE 2

| Scientific Name | Japanese Name | 1 | 2 | 3 | 4 | 5 |
|---|---|---|---|---|---|---|
| *Spinacia oleracea* | Hourensou | + | ++ | + | + | + |
| *Brassica rapa* var. *peruviridis* | Komatsuna | ++ | ++ | + | − | − |
| *Raphanus sativus* | Daikon | ++ | ++ | ++ | − | ++ |
| *Brassica oleracea* var. *capitata* | Kyabelu | ++ | ++ | ++ | − | n.d |
| *Brassica rapa* var. *chinensis* | Chingensai | ++ | ++ | ++ | + | ++ |

TABLE 2-continued

| Scientific Name | Japanese Name | 1 | 2 | 3 | 4 | 5 |
|---|---|---|---|---|---|---|
| *Brassica rapa* var. *glabra Regel* | Hakusai | ++ | ++ | − | − | + |
| *Brassica rapa* var. *nippo-oleifera* | Nanohana | ++ | ++ | − | − | − |
| *Zoysia japonica* | Shiba | + | ++ | ++ | ++ | n.d |
| *Oryza sativa* | Inc | ++ | ++ | ++ | ++ | ++ |
| *Zea mays* | Toumorokoshi | − | + | ++ | ++ | ++ |
| *Triticum aestivum* | Komugi | + | ++ | + | ++ | ++ |
| *Cucumis sativus* | Kyuri | ++ | + | ++ | ++ | ++ |
| *Chrysanthemum coronarium* | Syungiku | ++ | ++ | ++ | − | n.d |
| *Lactuca sativa* | Retasu | ++ | ++ | ++ | ++ | ++ |
| *Carthamus tinctorius* | Benibana | − | ++ | ++ | ++ | ++ |
| *Allium cepa* | Tamanegi | ++ | ++ | ++ | + | ++ |
| *Pisum sativum* | Endou | + | ++ | − | − | − |
| *Glycine max* | Daizu | ++ | ++ | + | + | ++ |
| *Vicia faba* | Soramame | ++ | ++ | ++ | ++ | ++ |
| *Allium fistulosum* | Negi | ++ | ++ | ++ | + | ++ |

Example 6

Figure 14:
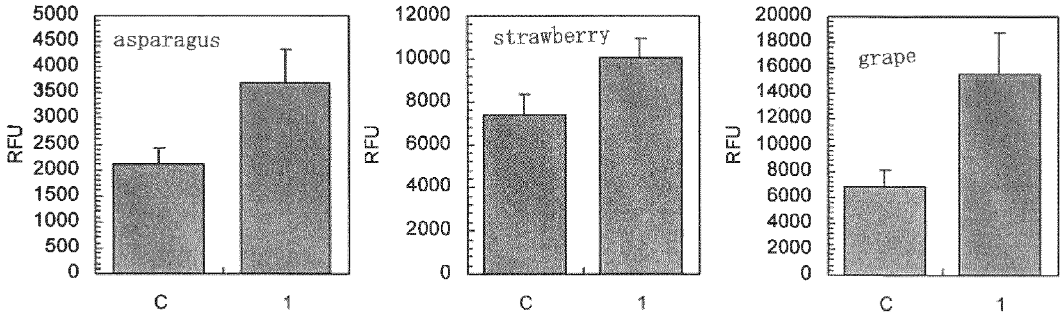
FIG. 14 shows the amount of reactive oxygen ($H_2O_2$) generated by an acidic heat-treated solution of *Corynebacterium* in asparagus, strawberries, and grapes. The acidic heat-treated solution was applied to the leaves of each plant and the amount of reactive oxygen generated was measured. Values are indicated in units of relative fluorescent units (RFU). The amount of the generated reactive oxygen is shown after treatment with the following: C) a control, or 1) a solution (100 ppm) after an acidic heat-treated solution of *Corynebacterium* was subjected to molecular fractionation (not less than 5 kDa and not more than 30 kDa).

Evaluation of the Induction of Disease Resistance by the Production of Reactive Oxygen as an Index in Asparagus, Strawberries, and Grapes Reactive oxygen was measured by the method described in Example 5. For asparagus, leaves were collected from the plants cultivated by the method described in Example 5 for one month, and the generation of reactive oxygen was measured. For strawberries and grapes, young plants were purchased and acclimatized by cultivating for 2- to 3-weeks at 25° C. in a green house. Then, healthy leaves were selected and collected, and the generation of reactive oxygen was measured. An acidic heat-treated solution of *Corynebacterium* fractionated to have a molecular weight of not less than 5 kDa and not more than 30 kDa by ultrafiltration was used for the treatment solution. In the ultrafiltration, an ultrafiltration filter (Amicon Ultra-15 centrifugal filter; 30K NMWL, 5K NMWL; Millipore) was used for molecular weight fractionation. Relative fluorescence intensity was measured as amount of reactive oxygen that was generated and compared with the control. As shown in FIG. 14, it was found that the fractionated solution also generated a significant amount of reactive oxygen during the treatment of asparagus, strawberries and grapes.

Example 7

Effect of Solution of *Corynebacterium* on Chitinase Activity in Cabbages

Figure 15:
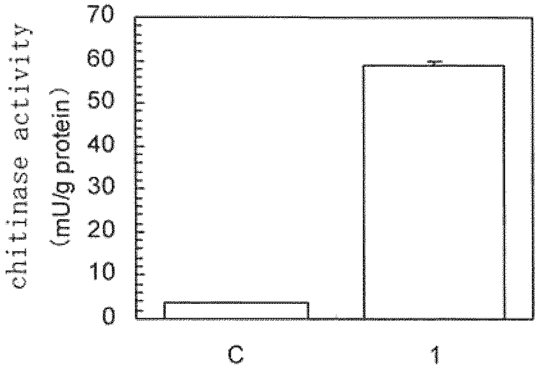
FIG. 15 shows the effect of an acidic heat-treated solution of *Corynebacterium* on the chitinase activity of cabbage. The treated solution was injected into leaves of cabbage. The cabbage seeds had been planted and then cultivated for 3 weeks before treatment. The chitinase activity at 48 hours after treatment was measured. The activity is shown for treatment of the following: C) control, or 1) an acidic heat-treated solution of *Corynebacterium.*

Cabbages were seeded in soil and cultivated for 3 weeks. Thereafter, the first true leaf was injected with a 10-fold diluted acidic heat-treated solution of *Corynebacterium.* 48 hours later, the chitinase activity was measured. The control group was subjected to a water treatment. As shown in FIG. 15, compared with that of the control, the chitinase activity was significantly increased by spraying the acidic heat-treated solution of the bacterial cells.

Example 8

Figure 16:
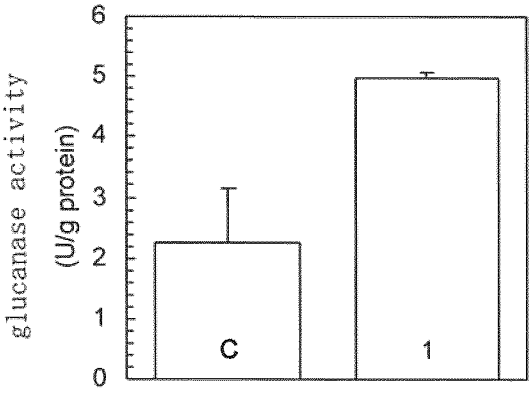
FIG. 16 shows the effect of an acidic heat-treated solution of *Saccharomyces cerevisiae* on the glucanase activity of rice. The activity is shown for treatment with the following: C) a control, or 1) an acidic heat-treated solution of *Saccharomyces cerevisiae.*
Figure 17:
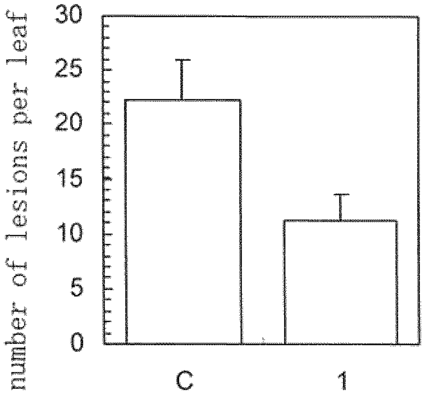
FIG. 17 shows the control effect of an acidic heat-treated solution of *Saccharomyces cerevisiae* on infection of rice blast. Pretreatment was done using the following: C) a control (spreading agent APPLAUCH BI (Kao Corporation)), or 1) an acidic heat-treated solution of *Saccharomyces cerevisiae* was added to the spreading agent. The y-axis of the graph indicates the number of the lesions per leaf.

Effect of Acidic Heat-Treated Solution of *Saccharomyces cerevisiae* on Rice In accordance with the method described in Example 4, the effect of the acidic heat-treated solution of *Saccharomyces cerevisiae* on rice was examined by measuring an increase in glucanase activity and the effect on infection. As shown in FIG. 16, it was found that spraying acidic heat-treated solution of *Saccharomyces cerevisiae* (2-fold dilution) significantly increased the glucanase activity. In addition, as shown in FIG. 17, spraying the acidic heat-treated solution of *Saccharomyces cerevisiae* (5-fold dilution) was able to control pathogenic infection significantly.

Example 9

Figure 18:
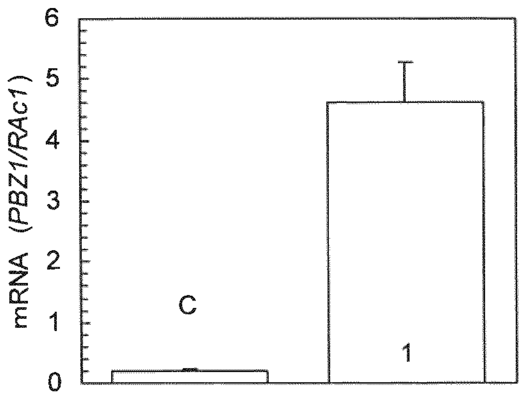
FIG. 18 shows the effect of inducing the expression of a disease resistance gene by treating rice roots with an acidic heat-treated solution of bacterial cells. The expression amount of the PBZ1 gene normalized with the expression amount of the RAc1 is shown with treatment of the following: C) a control, or 1) an acidic heat-treated solution of *Corynebacterium.*

Induction of Expression of Disease Resistance Gene by Treatment of Rice Roots with Acidic Heat-Treated Solution of Bacterial Cells A 1 mL tip filled with agar medium in which 0.8% Agar was added to OptMS inorganic salt culture medium (Table 1) was set on a tip rack. Sterilized rice seeds (variety: Koshihikari) were seeded in the medium. Part of the tip (about 20 mm and lower part from the bottom) was cut to allow the root to elongate. Cultivation was carried out for one week while the cut face was immersed in purified water to prevent drying. To rice seedlings grown on the tip, a styrene foam buoy with a thickness of 20 mm was attached. The tip with the buoy was then floated in a food container (C-AP Fruit 200, Chuo Kagaku Co., Ltd.) filled with 1 L of OptMS. The rice was cultivated under these conditions another week and rice having a foliar age of 4.5 true leaves, which had been cultured for two weeks in total, was used as the experimental material. A treated solution (100 mL) was put in the bottom of a Technopot (Sumitomo Bakelite Co., Ltd.), and the rice grown by hydroponics for 2 weeks was floated together with the styrene foam so that the root was sufficiently immersed in the treated solution. The acidic heat-treated solution of *Corynebacterium* was used at a concentration of 20%. The size of the styrene foam was adjusted in advance so as to fit in the Technopot. The cultivation was carried out in a constant-temperature plant incubator (Koitotron, Koito Industries, Ltd.) with a diurnal cycle of a 16-hour light period and a 8-hour dark period at a temperature of 28° C. and a light intensity of about 150 μmol $m^{-2}$ $s^{-1}$. Fifteen hours after the root was treated, sampling was carried out. The entire root was used as one sample. Total RNA was extracted from each sample using RNeasy Plant Mini Kit (QIAGEN). After the total RNA was subjected to DNase treatment using RNase free DNase Set (QIAGEN), reverse transcription was carried out using a reverse transcriptase, High Capacity cDNA Reverse Transcription Kit (Applied Biosystems) from an oligo dT primer. Then, quantitative PCR was performed using the synthesized single-strand cDNA as the template. The quantitative PCR was carried out using ABI PRISM 7500 with reaction conditions of 40 cycles of 95° C. for 15 seconds and 60° C. for 60 seconds. As a reagent, Power SYBR Green PCR Master Mix (Applied Biosystems) was used. For the genes to be quantified, RAc1 (RAP code, Os11g0163100) was used as a housekeeping gene and PBZ1 (RAP code, Os12g0555200) was used as a gene related to disease resistance. The following primers were used for expression of each gene: 5'-CCCCTTGTGTGTGACAATGG-3'(SEQ ID NO: 1) and 5'-CCCTGGGCGCATCGT-3'(SEQ ID NO: 2)(RAc1), 5'-GGAGCAGGAGAAGATGATCG-3'(SEQ ID NO: 3) and 5'-TTCTTCTCACATGCGACCAC-3'(SEQ ID NO: 4) (PBZ1). The expression amount of PBZ1 was normalized using the expression amount of RAc1. The results are shown in FIG. 18. When the root was treated, it was found that the expression amount of the PBZ1 gene increased in the root.

INDUSTRIAL APPLICABILITY

An inducer of disease resistance can be readily obtained by heat-treatment in an acidic solution (acidic heat-treatment) of various microorganism cell residues after amino acid fermentation, or the like, or microbial cells from organic sludge. Furthermore, since the effect is seen at a low concentration (for example, acidic heat-treatment of 200 mg/L of bacterial cells in dry weight), a large amount can be readily prepared for a low cost.

It is known that many pesticides, such as bactericides, act directly on plant pathogens and exhibit bactericidal effects against pathogens. Yet, their continuous use often causes the emergence of a resistancemutant to the pesticide agent. To the contrary, pesticides that induce resistance can be used over a long period of time with less possibility of the emergence of a drug resistance mutant. The acidic heat-treated solution of microbial cells prevents the infection of pathogens by inducing disease resistance rather than antibacterial activity, and thus there is less chance to generate a resistance mutant. Furthermore, it can be used over a long period of time, which means the enhancer of disease resistance is industrially very useful.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method comprising:

applying to a plant a composition comprising a microbial cell extract so that pathogenic infectious diseases of said plant are controlled, wherein said microbial cell extract has been subjected to a heat treatment temperature of 70° C. or higher in an acidic solution, wherein said acidic solution is at pH of 1 to 6, and wherein said microbial cell is selected from the group consisting of *Corynebacterium glutamicum, Pantoea ananatis, Bacillus subtilis*, and *Saccharomyces cerevisiae.*

2. The method according to claim 1, wherein said composition is a foliar spray agent.

3. The method according to claim 1, wherein said composition further comprises a metal salt.

4. The method according to claim 3, wherein the metal of said metal salt is selected from the group consisting of zinc, copper, and a combination thereof.

5. The method according to claim 1, wherein said heat treatment temperature is 100° C. or higher.

6. A method comprising:

applying to a plant a composition comprising a microbial cell extract so that pathogenic infectious diseases of said plant are controlled, wherein said microbial cell extract has been subjected to a heat treatment temperature of 70° C. or higher in an acidic solution, wherein said acidic solution is at pH of 1 to 6, and wherein said microbial cell is selected from the group consisting of *Pantoea ananatis, Bacillus subtilis*, and *Saccharomyces cerevisiae.*

7. The method of claim 6, wherein the microbial cell is *Saccharomyces cerevisiae.*

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1

ccccttgtgt gtgacaatgg                                    20


<210> SEQ ID NO 2
<211> LENGTH: 15
<212> TYPE: DNA
<213> ORGANISM: Artificial sequence
<220> FEATURE:
<223> OTHER INFORMATION: primer

<400> SEQUENCE: 2

ccctgggcgc atcgt                                         15


<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3

ggagcaggag aagatgatcg                                    20


<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4

ttcttctcac atgcgaccac                                    20
```